United States Patent
Berrettini

(10) Patent No.: US 6,831,153 B2
(45) Date of Patent: Dec. 14, 2004

(54) GENE AND METHODS FOR DIAGNOSING NEUROPSYCHIATRIC DISORDERS AND TREATING SUCH DISORDERS

(75) Inventor: Wade H. Berrettini, Haverford, PA (US)

(73) Assignee: Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 10/127,124

(22) Filed: Apr. 19, 2002

(65) Prior Publication Data

US 2002/0168675 A1 Nov. 14, 2002

Related U.S. Application Data

(63) Continuation of application No. 09/689,423, filed on Oct. 12, 2000, now Pat. No. 6,414,131.
(60) Provisional application No. 60/195,620, filed on Apr. 7, 2000, and provisional application No. 60/159,354, filed on Oct. 14, 1999.

(51) Int. Cl.⁷ .......................... C07K 1/00; C07K 14/00; C07H 21/02; G01N 33/53
(52) U.S. Cl. ........................ 530/350; 536/23.1; 435/7.1
(58) Field of Search ........................ 530/350; 536/23.1; 435/7.1, 6; 514/2

(56) References Cited

U.S. PATENT DOCUMENTS

| | | | |
|---|---|---|---|
| 5,866,412 A | 2/1999 | Chen et al. | 435/320.1 |
| 5,914,394 A | 6/1999 | Chen et al. | 536/23.5 |
| 5,939,316 A | 8/1999 | Chen et al. | 435/320.1 |
| 5,955,355 A | 9/1999 | Chen et al. | 435/320.1 |

OTHER PUBLICATIONS

Ausubel et al. (1989 Current Protocols in Molecular Biology, vol. I, Green Publishing Associates, Inc. and John Wiley & Sons, Inc. N.Y.

Berrettini et al., "Chromosome 18 DNA markers and manic–depressive illness:Evidence for a susceptibility gene", Proc. Natl. Acad. Sci. USA 1994 91:5918–5921.

Berrettini et al., "A Linkage Study of Bipolar Illness", Arch. Gen. Psychiatry 1997 54: 27–35.

Goldin et al., "Improvement of the Power to Detect Complex Disease Genes by Regional Inference Procedures", Genetic Epidemiology 1997 14:785–789.

Kalsi et al., "Linkage Analysis of Manic Depression (Bipolar Affective Disorder) in Icelandic and British Kindreds using Markers on the Short Arm of Chromosome 18" Hum. Heredity 1997 47:268–78.

Knowles et al., "No Evidence for Significant Linkage between Bipolar Affective Disorder and Chromosome 18 Pericentromeric Markers in a Large Series of Multiplex Extended Pedigrees", Am. J. Hum. Genet. 1998 62:916–24.

Lin et al., "Parental Transmission and D18S37 Allele Sharing in Bipolar Affective Disorder", Genetic Epidemiology 1997 14:665–8.

Nöthen et al., "Systematic Search for Susceptibility Genes in Bipolar Affective Disorder–Evidence for Disease Loci at 18p and 14p", Am. J. Hum. Genet. 1997 61(S) : A288.

Schwab et al., Support for a Chromosome 18p Locus Conferring Susceptibility to Functional Psychoses in Families with Schizophrenia,by Association and Linkage Analysis, Am. J. Hum. Genet. 1998 63: 1139–1152.

Schwab et al., "Evaluation of a susceptibility gene for schizophrenia on chromosome 6p by multipoint affected sib–pair linkage analysis", Nature Genetics 1995 11:325–327.

Stine et al., "Evidence for Linkage of Bipolar Disorder to Chromosome 18 with a Parent–of–Origin Effect", Am.J.Hum.Genet. 1995 57:1384–1394.

Primary Examiner—Olga N. Chernyshev
(74) Attorney, Agent, or Firm—Licata & Tyrrell P.C.

(57) ABSTRACT

A mammalian 22444 gene and gene products which are predictive of a susceptibility or predisposition to various neuropsychiatric disorders are provided. Methods of predicting an individual's susceptibility to developing or having a neuropsychiatric disorder via detection of these diagnostic markers are also provided. In addition, compositions and methods for identifying compositions for use in the treatment of neuropsychiatric disorders via these genes and gene products are described.

1 Claim, No Drawings

SEQUENCE LISTING

<160> NUMBER OF SEQ ID NOS: 2

<210> SEQ ID NO 1
<211> LENGTH: 3844
<212> TYPE: DNA
<213> ORGANISM: Homo sapiens

<400> SEQUENCE: 1

```
aattcgcatc taatagttgg agtgaatagt ctgcgaggga tttttagatc tgcttaattc      60
ttctggtcag catgcagtgg catatttaag gaggcaatgt tataaccctt taaaatgtaa     120
tcatatgcaa aattctatgt atgatttggg agaccccttt aaaattctct ctatgtatgt     180
aatcacagaa gccccaattt gaaaaagtac tcctgcaaca tgcttggaaa tatgccagtt     240
gaaacaagga tcaaggcaga aggctggcag aaatctacca ctctattatt tattccttag     300
aaagtctttc aaagaattgg gggcatattc acattttggg gtgaatattc acattttatt     360
```

```
ttcattgcac aaacttgaaa tgcatgaact cagggtacca ttcagcatca gcaacaaatc    420
agaagcagct cttggaaatg ttcaatgaga cctcccacgt ctcacttaga tctctgagaa    480
tcagagctgg aaggactctg aatatccatt ttggaggttg gtgacaggag aagacccacc    540
agcctcatca ctgtcagcat ctcaaagtca ctggtctttc atagtgcaca ggaagatgca    600
ctcacacgtc ctctcatcac atctctctag cactccagag gcattttttg gttaaccata    660
cttcattctt tctacttaga ctagttatta tcatctgaat acattcacca cctacctcca    720
acctatgtgc atcccatttt aaataggtta cttcctaaac tctaactata gccacaggct    780
tcatatttaa ttttcagttc cttccagctc ttttcatcag agcgaattca tttctgtatc    840
ctttgctctg gaccctgtca aaagttgcga ccatttctga ttacaactgt tgtagcctgt    900
gagggaagca gccttctcac ccagaaaccc atctgactgt ccagcccag ttcagagctc      960
ccgtcccacc ccggcagaaa cttctcctac cttctcatgg attccaaggt ctttttgctc    1020
ctttgttgct ggatggtcag gaactcagtg tgtccttcca ccacgctctt caccccacca    1080
cattccaggc cagcaaccac catgccaaaa ctgcattgta ctttccaaac caggcctcag    1140
gcaatggcag ggaattcctg cctccaggct cccaagtctc tccagctccc agagggtccc    1200
ttccctttgt tccttcccct ctggagccag ctccacaccc ttggccaact caccaacctt    1260
ctggtgcgca gtagcacctc ccagagcttg cagcacctat tccaaagaca ccactggctg    1320
atcagggtcc ctttggcctc tcaatagccc tgtcacctgg gccatacctc tgcagagcca    1380
ggagcagttg acattctttt ttttttttt gagacggagt ctcactctat cgcccaggct     1440
ggagtgcagt ggtgtgatct cggctcacta caacctctgc ctcccgggtt caagcgattc    1500
tcctgcctca gcctcccaag tagctgggat tacaggcatg cgtgccacca cacctggcta    1560
atttttgtag ttttcgtaga cagggtttca caatgttgg ctaggttgg tctcaaactc      1620
ctgacctcag gcgatccacc cacctccacc tcccaaagtg ctgggattaa aggcgtgcac    1680
cactgcacct ggctaacatt ctttaatgac tgcacaccag acaatgcagt cacagacacc    1740
actcccatag cctgtttccc ttggcttcca gggaaatgac tcattcatga cagttgaggt    1800
cacagttgcc cccactgttt cctatcgcta tgaaaggcca tcccaaacac cagcagatcc    1860
actcctgccc ctttgtgtat tctgcttctg ggttacttgc cctgggggtg ccaaacccaa    1920
gttcatgggt gaaggctgcc aaaatgtcat tccatggcca tgcctcagtt ttggccacta    1980
gggactgtct ctagctttcc aaaaggaagg agttaagatg tccaaggaaa ttatggagtc    2040
ttactgtctt tggccaagtg gttcctaaaa tggacccctt ttgacctctg tagggaagga    2100
aaaagaactt ccctctcttcc cattaggttc tgtagctgag tgaactaaca aagacggatt    2160
aacaggagga aagcatacac atttttattta atattttac atgcacacgg gaactttcat    2220
aagaaaaatg aagacccaaa gaagctgtta ggaccgagag ctaatatacc cttttaacaa    2280
aagatgataa atttatggag aagtgacaca ggagaaaggt tcaagtttct aggggcagtc    2340
attgtgggc agtgactaat gaaagacaag ggttattttg gtgggtttgt acagatcagt     2400
ttcagggtgg actccgaacc cctggtgata agaacattct cctcttcctg gtacagggca    2460
ggcacgtttc ttagggaaga tttcatgacc tgcttttt gg acagagcgg gaggtcagcc    2520
agccagccag ccttgcagct gaggcttctc aagtgccttc agctacaatt agtcaacatg    2580
ctgaagggct cattgtgggg tggcgttttg tgttctgaac cgtttcgtct ccctcttgcc    2640
cacactgagg ttcacaggcg cctgcagagg agctggtgtg ggacgatggg gagattggga    2700
```

```
ggcaacatcg cctcctctgc atgaaatgct catgggcaca tgtctgctgc ctctacctac    2760
caaaggacag aaccagccaa ctggcatggc aggcagggag ccagcgcagc ctccaggccg    2820
tccatcctct ctcctcagta ccagggcctc ccgtcaacgc cagcgccaac agagagcctg    2880
ggcccccccg acccctccct cctgctggct ccttcttcct tctagggccc ctgctgcccc    2940
tctgtctcca gaattgtccc ctgcttgcca tttaacccat tcccagtgct tgttggtccc    3000
cgagggaccc agcctctcag ccctcaatgg tcacctgtcc cagccgcgga aggagaaggg    3060
gacagaggac actggttcat tccaccatat ttactgggc caggcctgca ctaggtgctg      3120
gggactccca ggtggacaag acagagacct gccctgaggg cctaacatgt tagtggagaa    3180
gataaataac aacagatcaa ccaagagtca gtgggaaacg tgcagcctgg atagatgcct    3240
tggtaaagcc aggctggcac agagagggcg gtggaggcct gtgcagggcc cgtggtcact    3300
caggagaggg agctgggcgg cctcccagct ccctctcgga agggtcatca cccaagagcg    3360
gcgcacagcc ttccttggct cccatcctgc cttgtgtggg acacagtggg cgccaggcag    3420
atctgacacc aacaggcgtc gccaggtttg ccagcacaca cactcaaata tgcacactca    3480
cgttctcgct ctcgcacact ttccgcacat actctcacac tcaccttac acttttacac      3540 atttactctt gcacaccaca tactcgctct ccacactcag tcgctcttac acatattcac    3600
gcagtcatac acacacacac acacacacac acacacacac aacatctgga tttgattagg    3660
aaactaaagg gacatctgtc accttccatg ttttgtttac attgcaacac attcttgtac    3720
tcgcttagcc ttggacggga ggctccatgc tctctcccag tttctgagta gctcccaccc    3780
ccagcgctgt ggcagtggag aagagagggg agagaaggca acattaaaaa aaaaaaaaaa    3840
aagg                                                                  3844
```

<210> SEQ ID NO 2
<211> LENGTH: 116
<212> TYPE: PRT
<213> ORGANISM: Homo sapiens

<400> SEQUENCE: 2

```
Met Asp Ser Lys Val Phe Leu Leu Leu Cys Cys Trp Met Val Arg Asn
  1               5                  10                  15

Ser Val Cys Pro Ser Thr Thr Leu Phe Thr Pro Pro His Ser Arg Pro
                 20                  25                  30

Ala Thr Thr Met Pro Lys Leu His Cys Thr Phe Gln Thr Arg Pro Gln
             35                  40                  45

Ala Met Ala Gly Asn Ser Cys Leu Gln Ala Pro Lys Ser Leu Gln Leu
         50                  55                  60

Pro Glu Gly Pro Phe Pro Leu Phe Leu Pro Leu Trp Ser Gln Leu His
 65                  70                  75                  80

Thr Leu Gly Gln Leu Thr Asn Leu Leu Val Arg Ser Ser Thr Ser Gln
                 85                  90                  95

Ser Leu Gln His Leu Phe Gln Arg His His Trp Leu Ile Arg Val Pro
                100                 105                 110

Leu Ala Ser Gln
            115
```

GENE AND METHODS FOR DIAGNOSING NEUROPSYCHIATRIC DISORDERS AND TREATING SUCH DISORDERS

INTRODUCTION

This application is a continuation of U.S. patent application Ser. No. 09/689,423, now U.S. Pat. No. 6,414,131 filed Oct. 12, 2000, which claims the benefit of U.S. Provisional Application No. 60/159,354, filed Oct. 14, 1999 and U.S. Provisional Application No. 60/195,620 filed Apr. 7, 2000. This invention was supported in part by funds from the U.S. government (NIMH grant MH59533) and the U.S. government may therefore have certain rights in the invention.

FIELD OF THE INVENTION

The present invention relates to the mammalian gene 22444, a novel gene associated with the susceptibility of an individual for developing or having a neuropsychiatric disorder such as schizophrenia, schizoaffective disorder or serious mood disorders including bipolar disorder and recurrent unipolar disorder. The present invention encompasses 22444 nucleic acids, recombinant DNA molecules, cloned genes and variants thereof, 22444 gene products, cloning vectors containing mammalian 22444 gene molecules and host cells genetically engineered to express these molecules. The present invention also relates to methods of identifying compounds which modulate expression of 22444 and to the use of these compositions as therapeutic agents in the treatment of these neuropsychiatric disorders. In addition, the present invention relates to methods for diagnostic evaluation, genetic testing and prognosis of neuropsychiatric disorders associated with the 22444 gene. Identification of individuals with mutations in the sequences of the 22444 gene of the present invention is useful as a diagnostic aide for various neuropsychiatric disorders, and in particular schizophrenia, schizoaffective disorders, bipolar disorder and recurrent unipolar disorder.

BACKGROUND OF THE INVENTION

Historically, schizophrenia (SZ) and bipolar (BP) disorder have been considered as non-overlapping nosological entities, with distinctive clinical characteristics, unique treatment regimens and separate (albeit unknown) etiologies.

The schizophrenic disorders are a group of syndromes manifested by massive disruption of thinking, mood, and overall behavior as well as poor filtering of stimuli. Diagnosis of schizophrenic disorder is currently based upon the presence of a number of behavioral characteristics of at least six months duration including: slowly progressive social withdrawal usually often accompanied by a deterioration in personal care; loss of ego boundaries with the inability to perceive oneself as a separate entity; loose thought associations, often with slowed thinking or overinclusive and rapid shifting from topic to topic; autistic absorption in inner thoughts and frequent sexual or religious preoccupations; auditory hallucinations, often of a derogatory nature; and delusions, frequently of grandiose or persecutory nature. Frequent additional signs include: flat effect and rapidly alternating mood shift irrespective of circumstances; hypersensitivity to environmental stimuli, with a feeling of enhanced sensory awareness; variability or changeable behavior incongruent with the external environment; concrete thinking with the inability to abstract; inappropriate symbolism; impaired concentration worsened by hallucinations and delusions; and depersonalization, wherein one behaves like a detached observer of one's own actions. Diagnosis of a schizophrenic disorder based upon these behaviors can thus be quite arbitrary and is influenced by sociocultural factors and schools of psychiatric thought. At present, there is no laboratory method for confirmation of a diagnosis of schizophrenia.

Bipolar disorder, also known as manic-depressive illness, involves cycles of mania and depression. Signs and symptoms of mania include: extreme irritability and distractibility; excessive euphoric feelings; a sustained period of behavior that is different from the usual behavior; increased energy activity, restlessness, racing thoughts and rapid talking; decreased need for sleep; unrealistic beliefs in one's abilities and powers; uncharacteristically poor judgment; increased sexual drive; abuse of drugs, particularly cocaine, alcohol and sleeping medications; obnoxious, provocative or intrusive behavior and denial that anything is wrong. Signs and symptoms of depression include: persistent sad, anxious or empty mood; feeling of hopelessness or pessimism; feeling of guilt, worthlessness or helplessness; loss of interest or pleasure in ordinary activities; decreased energy, a feeling of fatigue or of being "slowed down"; difficulty concentrating, remembering and making decisions; restlessness and irritability; sleep disturbances; loss of appetite and weight, or weight gain; chronic pain or other persistent bodily symptoms that are not caused by physical disease; and thoughts of death or suicide. Most people with manic-depressive illness can be helped with treatment. However, manic-depressive illness, which is currently diagnosed by symptoms alone, is often not recognized by the patient, relatives, friends and even physicians. If left untreated, bipolar disorder tends to worsen, and the person experiences episodes of full-fledged mania and clinical depression.

Accordingly, there is a need for better, more definitive diagnostic markers and methods for diagnosing neuropsychiatric disorders including schizophrenia and bipolar disorder and other related disorders.

U.S. Pat. No. 5,866,412 discloses a mammalian gene, fsh15w6, which is associated with bipolar affective disorder in humans. U.S. Pat. No. 5,914,394 discloses a mammalian gene fsh16, which is associated with bipolar affective disorder. U.S. Pat. No. 5,939,316 discloses a mammalian gene, fsh22, which is associated with bipolar affective disorder. U.S. Pat. No. 5,955,355 discloses a mammalian gene, fsh05, which is associated with bipolar affective disorder.

In the present invention, a new mammalian gene associated with neuropsychiatric disorders, referred to herein as 22444, has been identified.

SUMMARY OF THE INVENTION

The object of the present invention is to identify genes associated with neuropsychiatric disorders, to provide methods of treating and diagnosing neuropsychiatric disorders, and to provide methods for identifying compounds for use in these therapeutic and diagnostic methods.

In particular, an object of the present invention is to provide a mammalian gene, 22444, which is associated with neuropsychiatric disorders including schizophrenia, schizoaffective disorder and serious mood disorders including bipolar disorder and recurrent unipolar disorder, and nucleic acid sequences, recombinant DNA molecules, cloned genes and variants thereof, of 22444.

Another object of the present invention is to provide mammalian 22444 gene products and antibodies immunospecific for these 22444 gene products, or fragments or variants thereof.

22444 nucleic acid sequences and amino acid sequences are disclosed herein. Accordingly, another object of the present invention is to provide vectors, preferably expression vectors, comprising mammalian 22444, and host cells genetically engineered to express mammalian 22444 gene products.

Another object of the present invention is to provide methods of use of the 22444 gene and 22444 gene products for the diagnostic evaluation, genetic testing and prognosis of a neuropsychiatric disorder. For example, in one embodiment, a method is provided for predicting the susceptibility or predisposition of an individual to having or developing neuropsychiatric disorders including schizophrenia, schizoaffective disorder and serious mood disorders such as bipolar disorder and recurrent unipolar disorder by detecting for the presence or absence of the 22444 gene of gene product or mutations. In this method, the absence of the 22444 gene or gene product or the presence of a mutation thereof is predictive of susceptibility or predisposition of an individual to having or developing one of these neuropsychiatric disorders. In another embodiment, a method is provided for diagnosing neuropsychiatric disorders such as schizophrenia, schizoaffective disorder, and serious mood disorders including bipolar disorder and recurrent unipolar disorder in an individual by analyzing for the presence or absence of the 22444 gene or gene product or a variant thereof in a biological sample obtained from the individual. In this method, the absence of the 22444 gene or gene product or the presence of a variant thereof is indicative of the individual having a neuropsychiatric disorder.

Another object of the present invention is to provide new treatments and methods of identifying new treatments for neuropsychiatric disorders. In one embodiment, these treatments involve modulation of the expression of the mammalian 22444 gene and/or the activity or synthesis of a mammalian 22444 gene product. In another embodiment, treatments involve supplying the mammal with a nucleic acid molecule encoding normal 22444. Methods for identifying new treatments involving modulation of the expression of the 22444 gene and/or the synthesis or activity of 22444 gene products comprise contacting a compound to a cell that expresses a 22444 gene, measuring the level of 22444 gene expression, gene product expression or gene product activity produced by the cell and comparing this level to the level of 22444 gene expression, gene product expression or gene product activity in the cell in the absence of the compound. Compounds which alter the level of 22444 gene expression, gene product expression or gene product activity are thus identified as modulators of 22444 gene expression or gene product synthesis or activity.

DETAILED DESCRIPTION OF THE INVENTION

A review of genetic epidemiology and recent molecular linkage studies has revealed a high degree of concordance for schizophrenia genetics and bipolar disorder genetics. Specifically, genetic epidemiologic studies have revealed that relatives of bipolar (BP) probands are at increased risk for recurrent unipolar (RUP), BP and schizoaffective (SA) disorders, while relatives of schizophrenia (SZ) probands are at increased risk for SZ, SA and RUP disorders. The overlap in familial risk is believed to reflect shared genetic susceptibility. Recent genetic linkage studies have defined confirmed susceptibility loci for BP disorder for multiple regions of the human genome, including 4p16, 12q24, 18p11.2, 18q22, 21q21, 2²q11–13 and Xq26. Studies of SZ kindreds have yielded robust evidence for susceptibility at 18p11.2 and 22q11–13, both of which are implicated in susceptibility to BP disorder. Similarly, confirmed SZ vulnerability loci have been mapped to for 6p24, 8p and 13q32. Strong statistical evidence for a 13q32 BP susceptibility locus has been reported. Thus, both family and molecular studies of these disorders suggest shared genetic susceptibility. Accordingly, these two group of disorders may not be so distinct as current nosology suggests.

Significant evidence for a BP susceptibility locus on chromosome 18 using affected sibling pair (ASP) and affected pedigree member (APM) methods ($p=10^{-4}-10^{-5}$), obtained in 22 Caucasian kindreds of European ancestry has been reported (Berrettini et al. *Proc. Natl Acad. Sci. USA* 1994 91:5918–5921; and Berrettini et al. *Arch. Gen. Psychiatry* 1997 54: 32–39). Evidence for linkage appears to be more prominent in those families with paternally transmitted illness (Stine et al., *Am. J. Hum. Genet.* 1995 57:1384–1394; Gershon et al. *Neuropsychiatric Genetics* 1996 67:1–8; Nothen et al. *Molecular Psychiatry* 1999 4:76; Knowles et al. *Am. J. Hum. Genet.* 1998 62:916–24).

Genetic Analysis Workshop 10 (Goldin et al. *Genetic Epidemiology* 1997 14:563–8) allowed statistical geneticists to analyze data from Berrettini et al. *Arch. Gen. Psychiatry* 1997 54: 32–39; Nothen et al. *Am. J. Hum. Genet.* 1997 61(S): A288; Stine et al. *Am. J. Hum. Genet.* 1995 57:1384–1394; Knowles et al. *Am. J. Hum. Genet.* 1998 62:916–24; and Kalsi et al. *Hum. Heredity* 1997 47:268–78. Results of several different analyses were consistent with the existence of a BP susceptibility gene. For example, the entire data set of 382 affected sibling pairs (assuming BP, SA and RUP as affected) was analyzed using a non-parametric method (Lin, J. P. and Bale, S. J. *Genetic Epidemiology* 1997 14:665–8). At D18S37, for 382 affected sibling pairs excess allele sharing (58%) was evident, with $p=2.8\times10^{-8}$. Thus, there is a confirmed BP susceptibility locus on chromosome 18p11.2.

Approximately 20 chromosome 18 markers were employed in a linkage study of 59 multiplex German and Israeli schizophrenic (SZ) pedigrees, in which there were 24 affective disorder cases (2 were BP)(Schwab et al. Am. J. Hum. Genet. 1998 63: 1139). When these data were analyzed in two-point parametric methods, the maximum lod score was 3.1 at D18S53. A multipoint non-parametric analysis revealed LOD=2.9, p=0.0002, at D18S53. The SZ kindreds studied for 18p11 linkage are not nosologically or genetically distinct from other multiplex SZ kindreds. For example, these kindreds show linkage to chromosome 6p (Schwab et al. Nature Genetics 1995 11:325–7), as reported in other series of multiplex SZ kindreds (Straub et al. Nature Genetics 1995 11:287–93; Moises et al. Nature Genetics 1995 11:321–4). Nosological mis-classification does not explain the chromosome 18p11.2 linkage to SZ detected by Schwab et al. Am. J. Hum. Genet. 1998 63: 1139.

Thus, the 18p11.2 region has a confirmed BP susceptibility locus, and there is a statistically impressive report of linkage at this locus in SZ.

A susceptibility gene for neuropsychiatric disorders including SZ and BP has now been identified at the 18p11.2 susceptibility locus. Other neuropsychiatric disorders which are believed to be related to this gene include schizoaffective disorder and other serious mood disorders such as recurrent unipolar disorder. The isolated nucleotide sequence of this susceptibility gene is depicted in SEQ ID NO:1. This mammalian gene is referred to herein as 22444. The deduced amino acid sequence of a gene product encoded by this nucleic acid sequence is depicted in SEQ ID NO:2. The absence of this mammalian gene or an encoded gene product or the presence of variant gene or gene product thereof are believed to be indicative of the susceptibility of an individual to developing and/or having a neuropsychiatric disorder such as schizophrenia, schizoaffective disorder, or serious mood disorders including bipolar disorder and recurrent unipolar disorder. Accordingly, the present invention relates to the 22444 gene and 2244 gene products and their use as diagnostic markers for ascertaining susceptibility or predisposition of an individual to developing and/or having a neuropsychiatric disorder such as schizophrenia, schizoaffective disorder, or serious mood disorders including bipolar disorder and recurrent unipolar disorder. The 22444 genes and gene products and variants thereof are also useful in identifying new treatments and treating neuropsychiatric disorders.

As used herein by "22444 gene" it is meant a nucleic acid molecule containing the DNA sequence of SEQ ID NO:1; any DNA sequence that encodes a polypeptide containing the amino acid sequence comprising SEQ ID NO:2; and any DNA sequence that hybridizes to the complement of the DNA sequences that encode an amino acid sequence comprising SEQ ID NO:2 under moderately stringent conditions. By "moderately stringent conditions" it is meant conditions such as those described by Ausubel et al. (1989 Current Protocols in Molecular Biology, Vol. I, Green Publishing Associates, Inc. and John Wiley & Sons, Inc. N.Y.). As used herein, "22444 gene" also refers to degenerate variants encoding 22444 gene products. 22444 genes can include both genomic DNA or cDNA and mRNA transcribed by the genomic DNA.

The present invention also relates 22444 gene products. By "22444 gene products" it is meant to include amino acid sequences encoded by the normal and variant 22444 genes. This term is also meant to include functionally equivalent 22444 gene products. By "functionally equivalent" it is meant a gene product with at least one biological activity which is the same as the normal 22444 gene product. Accordingly, contacting cells with a functionally equivalent 22444 gene product can inhibit or delay the onset of one or more symptoms of a neuropsychiatric disorder.

Also provided in the present invention are nucleic acid sequences, either DNA, RNA or a combination thereof which hybridize to the 22444 gene. Such hybridization may occur under moderately stringent conditions, or more preferably highly stringent conditions. Such conditions are well known in the art and discussed in detail in references such as Ausubel et al. (1989 Current Protocols in Molecular Biology, Vol. I, Green Publishing Associates, Inc. and John Wiley & Sons, Inc. N.Y.). These nucleic acid sequences can be used as probes in the detection of normal and variant 22444 genes. These nucleic acid sequences can also be used as antisense agents altering expression of normal or variant 22444 genes. The present invention also relates to vectors comprising 22444 genes and nucleic acid sequences which hybridize to the 22444 gene. In a preferred embodiment, the vectors are expression vectors with a regulatory element which directs expression of the 22444 gene or the nucleic acid sequence. The present invention also relates to host cells genetically engineered to express 22444 gene products.

22444 genes, 22444 gene products and variants thereof as well as nucleic acid sequences hybridizing to the 22444 gene are useful in diagnosing neuropsychiatric disorders, identifying new treatments for neuropsychiatric disorders and in treating neuropsychiatric disorders.

In one embodiment, individuals with a predisposition to developing or having a neuropsychiatric disorder such as schizophrenia, schizoaffective disorder, or serious mood disorders including bipolar disorder and recurrent unipolar disorder are identified by detecting variations in the 22444 gene of SEQ ID NO:1 or an absence of the 22444 gene of SEQ ID NO:1. Methods for identifying individuals with a known nucleotide sequence or variants thereof are well known in the art. Examples of such methods include, but are not limited, polymerase chain reaction (PCR), ligase chain reaction (LCR) and nucleic acid sequence based amplification (NASABA). Reverse-transcriptase PCR (RT-PCR) is also a powerful technique which can be used to detect the presence of a specific mRNA populations in a complex mixture of thousands of other mRNA species. In RT-PCR, an mRNA species is first reverse transcribed to complementary DNA (cDNA) with use of the enzyme reverse transcriptase; the cDNA is then amplified as in a standard PCR reaction. RT-PCR can thus reveal by amplification the presence of a single species of mRNA. Hybridization to clones or oligonucleotides arrayed on a solid support (i.e. gridding) can also be used to detect the presence of a selected nucleotide sequence.

In this method a DNA-containing biological sample is obtained from an individual. DNA or mRNA in the biological sample is then analyzed for the presence or absence of the 22444 gene of SEQ ID NO:1 or a variant thereof. The absence of the 22444 gene of SEQ ID NO:1 and/or the presence of a variant gene is indicative of the individual being susceptible to developing or having a neuropsychiatric disorder such as schizophrenia, schizoaffective disorder, or serious mood disorders including bipolar disorder and recurrent unipolar disorder.

Alternatively, biological samples obtained from an individual can also be analyzed for the presence of a variant 22444 gene product, such as those depicted in the presence or absence of the 22444 gene product of SEQ ID NO:2 to ascertain an individual's susceptibility to the neuropsychiatric disorders. Methods for detecting the presence or absence of a known polypeptide sequence are well known in the art. The 22444 gene product or variants and fragments thereof can be used to raise antibodies against the 22444 gene product or variant thereof. Such antibodies can then be used in various assays to detect the presence or absence of the 22444 gene product or variant thereof in a sample. Examples of these assays include, but are not limited to, radioimmunoassays, immunohistochemistry assays, competitive-binding assays, Western Blot analyses, ELISA assays, proteomic approaches, two-dimensional gel electrophoresis (2D electrophoresis) and non-gel based approaches such as mass spectrometry or protein interaction profiling. In these methods, the presence of a variant 22444 gene product or the absence of the 22444 gene product of SEQ ID NO:2 is indicative of an individual being susceptible to developing or having a neuropsychiatric disorder such as schizophrenia, schizoaffective disorder, or serious mood disorders including bipolar disorder and recurrent unipolar disorder.

The 22444 gene and 22444 gene products of SEQ ID NO:1 and SEQ ID NO:2 also provide useful tools for development of new treatments for these neuropsychiatric disorders. For example, as demonstrated herein mutations in the nucleotide sequence of SEQ ID NO:1 leads to variants with disrupted protein function in individuals with schizophrenia, schizoaffective disorder and serious mood disorders including bipolar and recurrent unipolar disorders. Accordingly, the 22444 gene product, agents which mimic the 22444 gene product or inhibit disruption in the function of the 22444 gene product may be useful in treating these neuropsychiatric disorders. Alternatively, agents which alter expression and/or levels of the normal protein may also be useful in the treatment of these disorders. Such agents can be identified in routine screening assays which examine levels of the 22444 gene or 22444 gene product as depicted in SEQ ID NO:1 and SEQ ID NO:2. Agents identified as altering levels and/or expression of the gene or gene product of SEQ ID NO:1 and SEQ ID NO:2 are expected to be useful in the treatment of these neuropsychiatric disorders.

The 22444 gene and 22444 gene products of SEQ ID NO:1 and SEQ ID NO:2 are also useful in identifying other proteins and/or genes encoding such proteins which interact with 22444 gene products. Various methods for identifying such proteins and/or genes for encoding these proteins are known in the art. Well known techniques include, but are not limited to, yeast two hybrid systems and receptor binding assays.

The following nonlimiting example is provided to further illustrate the present invention.

EXAMPLE

Genomic sequences from human chromosome 18, encoding the Golf(CA) repeat, as described by Berrettini et al. Psychiatric Genetics 1998 8:235–38, was used to generate genomic DNA sequence in the 5' direction within Golf intron 5. This sequence was analyzed for possible exons. Primers were designed from a possible exon in the new genomic sequence. These primers were then used to screen human brain cDNA libraries. Clones from these libraries were sequenced to reveal the nucleotide sequence depicted as SEQ ID NO:1. Variation in this sequence, which truncates the encoded polypeptide prematurely, has been found. It is believed that this premature truncation of the protein predisposes individuals to schizophrenia and serious mood disorders including bipolar and recurrent unipolar disorder.

Common sequence variants were also screened for with the entire 2.9 kb cDNA in DNA samples from 50 unrelated BP individuals and 50 unrelated persons with SZ. Direct sequencing of a 450 bp fragment, including the entire 22444 coding region, did not reveal a common polymorphism (minor allele frequency >5%). The coding region, ~25% of the 5'UTR and ~15% of the 3'UTR has been screened in a search for variants. One 5'UTR single nucleotide polymorphism (SP) was found which had a minor allele frequency of ~5%. A summary of the SNPs is given in the table below.

| bp^ | sequence | Restriction enzyme | allele cut | freq in EA* | freq in AA** |
|---|---|---|---|---|---|
| G2808T | CAGC(G/T)CAG | HhaI | G | 0.62 | 0.78+ |
| G3052A | CCGC(G/A)GAA | BstuI | G | 0.63 | 0.89# |
| G3072A | GAG(G/A)ACAC | MnlI | G | ND^^ | ND |
| G3117A | CACT(G/A)GGT | MaeI | A | ND | ND |
| A219G | CTGCA(A/G)CA | PstI | G | 0/034 | 0.12 |

^base pair from the cDNA of SEQ ID NO: 1;
^^ND, not determined.
*frequency of the cut allele in Americans of European ancestry (EA);
+Chi-square = 15.0, p = 0.0002, EA vs. AA frequency;
**frequency of the cut allele in Americans of African ancestry (AA);
Chi-square = 32.7, p < 0.00001, EA vs AA freq.

The G2808T and G3052A SNPs were genotyped in 171 unrelated individuals of European ancestry (EA). There was no deviation for Hardy-Weinberg equilibrium. Analysis of 48 African-Americans (AA) revealed significant differences in allele frequencies, compared to the EA group for G2808T and for G3052A. Analysis with the EH program revealed LD between these two SNPs (which are separated by 244 bp), with D =0.1 (Chi-square =14.7, p=0.005). Of the 171 unrelated EA individuals genotyped, 102 were SZ, while 69 were screened controls. There was LD between these SNPs and SZ.

| EH Program Output: | Locus/Allele | 1 | 2 |
|---|---|---|---|
| | Disease | 0.9000 | 0.1000 |
| | 1 | 0.6199 | 0.3801 |
| | 2 | 0.6345 | 0.3655 |

At these 3 loci, there are 8 possible haplotypes, listed below with their estimated frequencies.

| Allele at Disease | Allele at Marker 1 | Allele at Marker 2 | Independent | HALOTYPE FREQUENCY ASSUMING Markers Associated But Not Disease | Markers and Disease Associated |
|---|---|---|---|---|---|
| + | 1 | 1 | 0.353993 | 0.444062 | 0.321927 |
| + | 1 | 2 | 0.203883 | 0.113833 | 0.107816 |
| + | 2 | 1 | 0.217091 | 0.126991 | 0.149206 |
| + | 2 | 2 | 0.125033 | 0.215114 | 0.321051 |
| D | 1 | 1 | 0.039333 | 0.049340 | 0.078494 |
| D | 1 | 2 | 0.022654 | 0.012648 | 0.013306 |
| D | 2 | 1 | 0.024121 | 0.014110 | 0.008200 |
| D | 2 | 2 | 0.013893 | 0.023901 | 0.000000 |

| | | #param | Ln (L) | Chi-square |
|---|---|---|---|---|
| H0: | No Association | 2 | −297.09 | 0.00 |
| H1: | Markers Associated, independent of disease | 3 | −289.27 | 15.63 |
| H2: | Markers and Disease Associated | 6 | −283.37 | 27.43 |

This analysis assumes a 10% disease allele frequency, but the results are very similar if the disease allele frequency is increased to 60%. If the difference between the Chi-square values for H2 and H1 is the evidence for association with disease, then Chi-square=11.8, p=0.008.

What is claimed is:

1. An isolated mammalian 22444 gene product comprising an amino acid sequence of SEQ ID NO:2.

* * * * *